United States Patent
Sun et al.

(10) Patent No.: US 10,625,041 B2
(45) Date of Patent: Apr. 21, 2020

(54) CONNECTING VALVE STRUCTURE AND ANESTHETIC FILLING SYSTEM

(71) Applicant: SHENZHEN COLINN MEDICAL CO., LTD., Shenzhen, Guangdong (CN)

(72) Inventors: Xiangming Sun, Guangdong (CN); Jihong Zhu, Guangdong (CN); Fei Wo, Guangdong (CN)

(73) Assignee: SHENZHEN COLINN MEDICAL CO., LTD., Shenzhen, Guangdong (CN)

( * ) Notice: Subject to any disclaimer, the term of this patent is extended or adjusted under 35 U.S.C. 154(b) by 117 days.

(21) Appl. No.: 15/741,518

(22) PCT Filed: Oct. 20, 2017

(86) PCT No.: PCT/CN2017/107121
§ 371 (c)(1),
(2) Date: Jan. 3, 2018

(87) PCT Pub. No.: WO2019/000725
PCT Pub. Date: Jan. 3, 2019

(65) Prior Publication Data
US 2019/0083737 A1    Mar. 21, 2019

(30) Foreign Application Priority Data
Jun. 27, 2017   (CN) .......................... 2017 1 0502117

(51) Int. Cl.
*A61M 16/18*     (2006.01)
*A61J 3/00*      (2006.01)
(Continued)

(52) U.S. Cl.
CPC .............. *A61M 16/183* (2013.01); *A61J 3/00* (2013.01); *A61J 7/0053* (2013.01); *A61J 1/20* (2013.01); *A61M 39/10* (2013.01)

(58) Field of Classification Search
CPC .... A61M 16/183; A61M 39/10; A61M 39/18; A61M 2039/267; A61J 1/20;
(Continued)

(56) References Cited

U.S. PATENT DOCUMENTS

4,867,212 A * 9/1989 Mohr .................. A61M 16/183
141/290
5,505,236 A * 4/1996 Grabenkort ......... A61M 16/183
128/202.27
(Continued)

*Primary Examiner* — Craig J Price
*Assistant Examiner* — Andrew J Rost
(74) *Attorney, Agent, or Firm* — Rankin, Hill & Clark LLP (57) ABSTRACT

A connecting valve structure and an anesthetic filling system are provided. When a valve core assembly is in the open state, a pipe and a filling port are in seal fit, besides, the connecting ring, the seal pipe, and the drug guiding pipe are integrated as a whole, when the seal pipe is inserted into or pulled out of the filling port of the evaporator, no BHT exudate occurs. In addition, an inner pipe wall of the seal pipe, a surface of the connecting ring facing towards a first pipe end, and an outer pipe wall of the drug guiding pipe opposite to the seal pipe together form a pressure stabilizing groove which is used to equilibrate pressure in the container and the evaporator during the open state.

16 Claims, 6 Drawing Sheets

(51) Int. Cl.
*A61J 7/00* (2006.01)
*A61M 39/10* (2006.01)
*A61J 1/20* (2006.01)

(58) Field of Classification Search
CPC ...... A61J 1/2048; A61J 1/2003; A61J 1/2055; A61J 3/00; A61J 7/0053
USPC .............................................. 251/144, 149.9
See application file for complete search history.

(56) References Cited

U.S. PATENT DOCUMENTS

| | | | | |
|---|---|---|---|---|
| 5,799,711 | A * | 9/1998 | Heinonen | A61M 16/183 128/200.19 |
| 6,125,893 | A * | 10/2000 | Braatz | A61M 16/183 128/200.21 |
| 6,997,435 | B2 * | 2/2006 | Wrigley | B67D 7/0294 137/510 |
| 7,290,571 | B2 * | 11/2007 | Bunke | A61M 16/183 141/18 |
| 7,882,970 | B2 * | 2/2011 | Mitchell | A61M 16/183 215/40 |
| 8,500,088 | B2 * | 8/2013 | Freed | A61M 16/183 128/203.16 |
| 2007/0204932 | A1 * | 9/2007 | Freed | A61M 16/183 141/352 |
| 2016/0361514 | A1 * | 12/2016 | Warby | A61M 16/20 |

* cited by examiner

CONNECTING VALVE STRUCTURE AND ANESTHETIC FILLING SYSTEM

TECHNICAL FIELD

The present application relates to technical field of drug feeding structures, and more particularly to a connecting valve structure and an anesthetic filling system.

BACKGROUND ART

An anesthetic filling system is used to cooperate with an evaporator and comprises a container containing an anesthetic and a connecting valve structure with one end fixed at a drug outlet of the container, wherein another end of the connecting valve structure is inserted into a filling port of the evaporator. Generally, in order to ensure the sealing of the connection, an O-shaped ring is sheathed on an end part of the connecting valve structure, and an outer side wall of the connecting valve structure and an inner side wall of the filling port press the O-shaped ring. Due to the work requirement, multiple times of insertion and pulling of connecting valve structure into and out of the filling port of the evaporator are conducted, which further results in abrasion of the O-shaped ring and formation of impurities, besides, such O-shaped ring is generally made from (ethylene propylene diene monomer) EPDM material, during the friction of the insertion and pulling of the O-shaped ring into and out of the filling port, BHT exudate will occur, the BHT exudate will remain in the evaporator and be prone to be oxidized and yellowed in a high temperature state, which may result in trouble to users and make the users unnecessarily worry about the quality of the anesthetic, or even result in panic. In addition, because the O-shaped ring has a great process tolerance of design, which results in greater-insertion force during the insertion of the connecting valve structure into the evaporator, thus being inconvenient for medical staff to operate.

Technical Problem

An object of embodiments of the present application lies in that: in one respect, a connecting valve structure is provided in order to solve the problem in the prior art that the BHT exudate occurs during the friction of the insertion-pull between the filling port of the evaporator and the O-shaped ring, and the BHT exudate is easily oxidized and yellowed at the high-temperature state, and therefore bringing about worry of the users. Because the O-shaped ring has a great process tolerance of the design, which results in that during the insertion of the connecting valve structure into the evaporator, the insertion force increases and is not convenient for the general medical staff to operation.

In a second respect, an anesthetic filling system is provided to solve the problem in the prior art that the insertion-pull force is relatively great during the insertion-pull of the anesthetic filling system into and out of the evaporator, which is not convenient for the medical staff to operate and to solve the technical problem that the sealing effect between the anesthetic filling system and the evaporator is poor.

Technical Solution

In order to solve the above technical problem, the present application adopts the following technical solution:

In a first respect, the present application provides a connecting valve structure configured to connect an evaporator and a container containing an anesthetic so as to introduce the anesthetic to the evaporator, wherein the evaporator is provided with a filling port. The connecting valve structure comprises a drug guiding structure and a valve core assembly. The drug guiding structure comprises: a drug guiding pipe that is provided with a first pipe end configured to form an insertion fit with the filling port and a second pipe end communicating with an inner part of the container, a connecting ring that is integrally connected with an outer pipe wall of the drug guiding pipe and is formed by radially extending the outer pipe wall of the drug guiding pipe outwards, and a seal pipe that is integrally connected to the connecting ring and formed by extending an outer annular surface of the connecting ring towards the filling port of the evaporator. The seal pipe is in seal fit with the filling port when the drug guiding pipe is inserted into the filling port. The valve core assembly has an open state for opening the drug guiding pipe when the drug guiding pipe is inserted into the filling port and a closed state for blocking the drug guiding pipe when the drug guiding pipe is pulled out of the filling port.

In a second respect, the present application further provides an anesthetic filling system configured to connect with the evaporator to introduce the anesthetic to the evaporator. The anesthetic filling system comprises the container and the above-described connecting valve structure. The container comprises a cavity accommodated with the anesthetic and a drug outlet communicating with the cavity, the connecting valve structure is fixed at the drug outlet and in seal fit with the drug outlet.

Advantageous Effect

Compared with the prior art, the connecting valve structure provided by embodiments of the present application has the following advantages: when the valve core assembly is in the open state, that is, when the first pipe end, the connecting ring, and the seal pipe of the drug guiding pipe are all inserted in the filling port of the evaporator, the seal pipe and the filling port are in seal fit, besides, the connecting ring, the seal pipe, and the drug guiding pipe are integrated as a whole, in this way, when the seal pipe is inserted into or pulled out of the filling port of the evaporator, no BHT exudate occurs, that is, the O-shaped ring is excluded, and the yellowing of the anesthetic caused by the BHT exudate is completely solved, thereby enabling the user to use the drug more confidently. Furthermore, an inner pipe wall of the seal pipe, a surface of the connecting ring facing towards the first pipe end, and an outer pipe wall of the drug guiding pipe opposite to the seal pipe together form a pressure stabilizing groove which is used to equilibrate pressure in the container and the evaporator during the open state. The pressure stabilizing groove has functions in three respects: first, when the drug guiding structure is gradually inserts into the filling port of the evaporator, since both the evaporator and the container are sealed containers, internal air pressure gradually increases during the gradual insertion, while the pressure stabilizing groove can bear a part of the air pressure, thereby equilibrating the internal air pressure; second, by the arrangement of the pressure stabilizing groove, during the insertion of the drug guiding structure into the filling port, insertion difficulty due that the internal air pressure is greater than the atmospheric pressure will not occur, much less the difficulty in pulling out the drug guiding structure, thereby effectively decreasing the insertion-pull force between the drug guiding structure and the evaporator and being convenient for medical staff to operate; and third, when a part of the air pressure is borne by the pressure stabilizing groove, the inner pipe wall of the seal pipe has the trend to expand outwards as being oppressed by the internal air pressure, which further enhances the attachment tightness between the seal pipe and the filling port, thereby improving the sealing effect.

The anesthetic filling system provided by embodiments of the present application has the following advantages: when the above-described connecting valve structure is applied to the anesthetic filling system, the insertion-pull force between the connecting valve structure and the evaporator is effectively decreased, which is convenient for the medical staff to operate, and further improve the sealing property between the connecting valve structure and the drug filling system, thereby improving the transferring efficiency of the anesthetic.

DESCRIPTION OF DRAWINGS

In order to more clearly illustrate the technical solution in embodiments of the present application, the following drawings, which are to be used in the description of the embodiments or the prior art, will be briefly described. It will be apparent that the drawings described in the following description are merely embodiments of the present application. Other drawings may be obtained by those skilled in the art without paying creative labor.

Reference numerals in the drawings are listed as follows:

| | | | |
|---|---|---|---|
| Connecting valve structure | 1 | Drug guiding structure | 100 |
| Valve core assembly | 200 | Drug guiding pipe | 110 |
| First pipe end | 111 | Second pipe end | 112 |
| Connecting ring | 120 | Seal pipe | 130 |
| Pressure stabilizing groove | 101 | Sealing projection ring | 140 |
| Arc surface | 141 | Support base | 150 |
| Push member | 210 | Sealing structural member | 220 |
| Elastic member | 230 | Support | 240 |
| Open cavity | 241 | Perfusion mouth | 242 |
| Drug guiding channel | 201 | Push rod | 211 |
| Flow guide plate | 212 | Drainage chamber | 202 |
| Diversion chamber | 203 | First seal shim | 250 |
| First projection ring | 160 | Positioning block | 213 |
| positioning groove | 221 | Circular plate | 222 |
| guiding column | 223 | Flange | 170 |
| clasp | 180 | Annular slot | 243 |
| Second seal shim | 190 | Main plate | 171 |
| Second protrusion ring | 172 | Accommodation groove | 173 |
| Main support | 244 | Lug | 245 |
| Lid | 2 | Seal ring | 3 |
| Drug receiving port | 102 | Seal structure | 4 |

MODE FOR INVENTION

In order to make the purposes, technical solutions, and advantages of the present application clearer and more understandable, the present application will be further described in detail hereinafter with reference to the accompanying drawings and embodiments. It should be understood that the embodiments described herein are only intended to illustrate but not to limit the present application.

It should be noted that when an element is described as "fixed" or "arranged" on/at another element, it means that the element can be directly or indirectly fixed or arranged on/at another element. When an element is described as "connected" to/with another element, it means that the element can be directly or indirectly connected to/with another element.

It should also be understood that the same or similar reference numerals in the accompanying drawings of the embodiments of the present application correspond to the same or similar parts; in the description of the present application, it should be understood that if there are terms like "upper", "lower", "left", "right", etc., indicated directions or position relations are based on directions or positions presented in the drawings, and these terms are merely for the purpose of facilitating the description of the present application and simplified description, rather than indicating or implying that the device or element must have the specific directions and constructed or operated in specific directions. Thus, terms concerning to description of the position relation in the drawings are for illustrative purposes only but not to be understood as limiting of the scope of the present application, and the specific meaning of the above terms can be understood by one of ordinary skill in the art according to the specific conditions.

It should be understand that terms like "first" and "second" are only used for the purpose of description, and will in no way be interpreted as indication or hint of relative importance or implicitly indicate the number of the referred technical features. Thus, the features prefixed by "first" and "second" will explicitly or implicitly represent that one or more of the referred technical features are included. In the description of the present application, "multiple"/"a plurality of" refers to the number of two or more than two, except for clear and particular restriction.

Please refer to FIGS. 1-5, the present application provides a connecting valve structure, which is configured to connect an evaporator 5 and a container 6 containing an anesthetic in order to introduce the anesthetic to the evaporator 5, and the evaporator 5 is provided with a filling port 51; it should be noted that the connecting valve structure 1 is not limited to be used in the drug filling system, the connecting valve structure 1 can also be selected when other liquids requires to be sealed and transferred to another container 6. It should be explained that the connecting valve structure 1 is primarily applied in transferring desflurane, which is one kind of anesthetics and has a boiling point of 22.8° C., approaching the room temperature, and it is therefore indicated that a part of the desflurane presents in a gas state in the room temperature, the desflurane therefore should be contained in a specialized evaporator for use. The connecting valve structure 1 comprises a drug guiding structure 100 and a valve core assembly 200. The drug guiding structure 100 comprises: a drug guiding pipe 110 that is provided with a first pipe end 111 configured to be in insertion fit with the filling port 51 and a second pipe end 112 communicating with an inner part of the container 6, a connecting ring 120 that is integrally connected with an outer pipe wall of the drug guiding pipe 110 and is formed by radially extending the outer pipe wall of the drug guiding pipe outwards, and a seal pipe 130 that is integrally connected to the connecting ring 120 and formed by extending an outer annular surface of the connecting ring 120 towards the filling port 51 of the evaporator 5. The seal pipe 130 is in seal fit with the filling port 51 when the drug guiding pipe 110 is inserted into the filling port 51. The valve core assembly 200 has an open state for opening the drug guiding pipe 110 when the drug guiding pipe 110 is inserted into the filling port 51 and a closed state for blocking the drug guiding pipe 110 when the drug guiding pipe 110 is pulled out of the filling port 51.

In this embodiment, when the valve core assembly 200 is in the open state, that is, when the first pipe end 111, the connecting ring 120, and the seal pipe 130 of the drug guiding pipe 110 are all inserted into the filling port 51 of the evaporator 5, the seal pipe 130 and the filling port 51 are in seal fit, besides, the connecting ring 120, the seal pipe 130, and the drug guiding pipe 110 are integrated as a whole, in this way, when the seal pipe 130 is inserted into or pulled out of the filling port 51 of the evaporator 5, no BHT exudate occurs, that is, the O-shaped ring is deleted, and the yellowing of the anesthetic resulted from the BHT exudate is completely solved, thereby enabling the user to use the drug more confidently. Furthermore, an inner pipe wall of the seal pipe 130, a surface of the connecting ring 120 facing towards the first pipe end 111, and an outer pipe wall of the drug guiding pipe 110 opposite to the seal pipe 130 together form a pressure stabilizing groove 101 which is used to equilibrate pressure in the container 6 and the evaporator 5 during the open state. The pressure stabilizing groove 101 has functions in three respects: first, when the drug guiding structure 100 is gradually inserts into the filling port 51 of the evaporator 5, since both the evaporator 5 and the container 6 are sealed containers, internal air pressure gradually increases during the gradual insertion, while the pressure stabilizing groove 101 can bear a part of the air pressure, thereby equilibrating the internal air pressure; second, by the arrangement of the pressure stabilizing groove 101, during the insertion of the drug guiding structure 100 into the filling port 51, insertion difficulty due that the internal air pressure is greater than the atmospheric pressure will not occur, much less the difficulty in pulling out the drug guiding structure 100, thereby effectively decreasing the insertion-pull force between the drug guiding structure 100 and the evaporator 5 and being convenient for medical staff to operate; and third, when a part of the air pressure is borne by the pressure stabilizing groove 101, the inner pipe wall of the seal pipe 130 has the trend to expand outwards or expand as being oppressed by the internal air pressure, which further enhances the attachment tightness between the seal pipe 130 and the filling port 51, thereby improving the sealing effect.

Please refer to FIGS. 2-5, further, the drug guiding structure 100 further comprises a sealing protection ring 140 that is integrally connected to an outer pipe wall of the seal pipe 130 and is formed by radially extending the outer pipe wall of the seal pipe 130 outwards, a shape of a cross section of the sealing projection ring 140 has a convex curve that is convex to a direction away from the seal pipe 130. In this embodiment, the convex curve is an arc. The sealing projection ring 140 has an arc surface 141. The seal pipe 130 and the sealing projection ring 140 together form a sealing structure that is in seal fit with the filling port 51 in the open state.

In this embodiment, because inclining situations inevitably occur during the insertion fit between the drug guiding structure 100 and the filling port 51 of the evaporator 5, the arrangement of the arc surface 141 is able to prevent stuck phenomenon even the drug guiding structure 100 is inclined to any direction, thus ensuring fluent insertion fit and improving the efficiency of the insertion fit.

Figure 2:
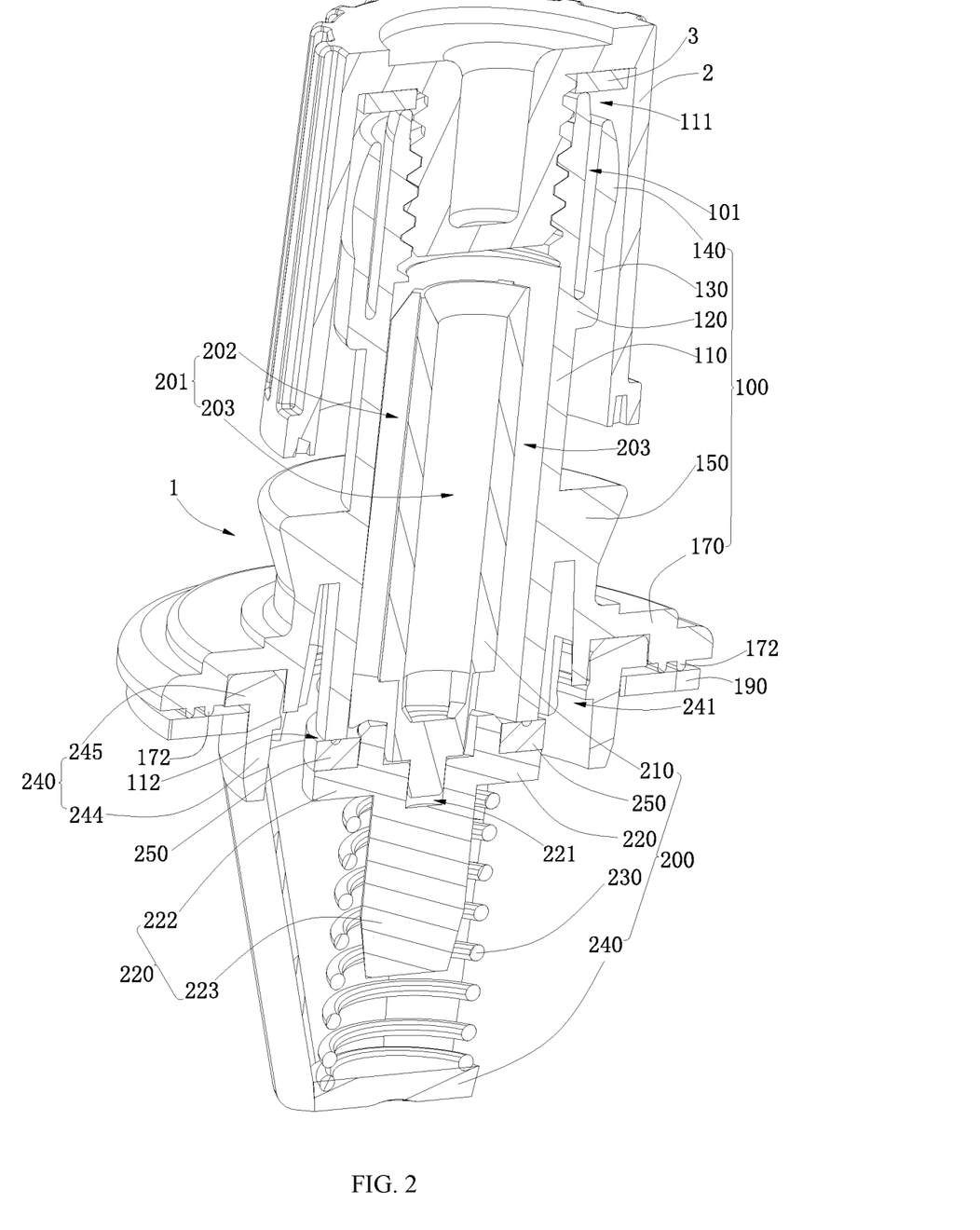
FIG. 2 is a sectional view taken from line A-A of FIG. 1.
Figure 3:
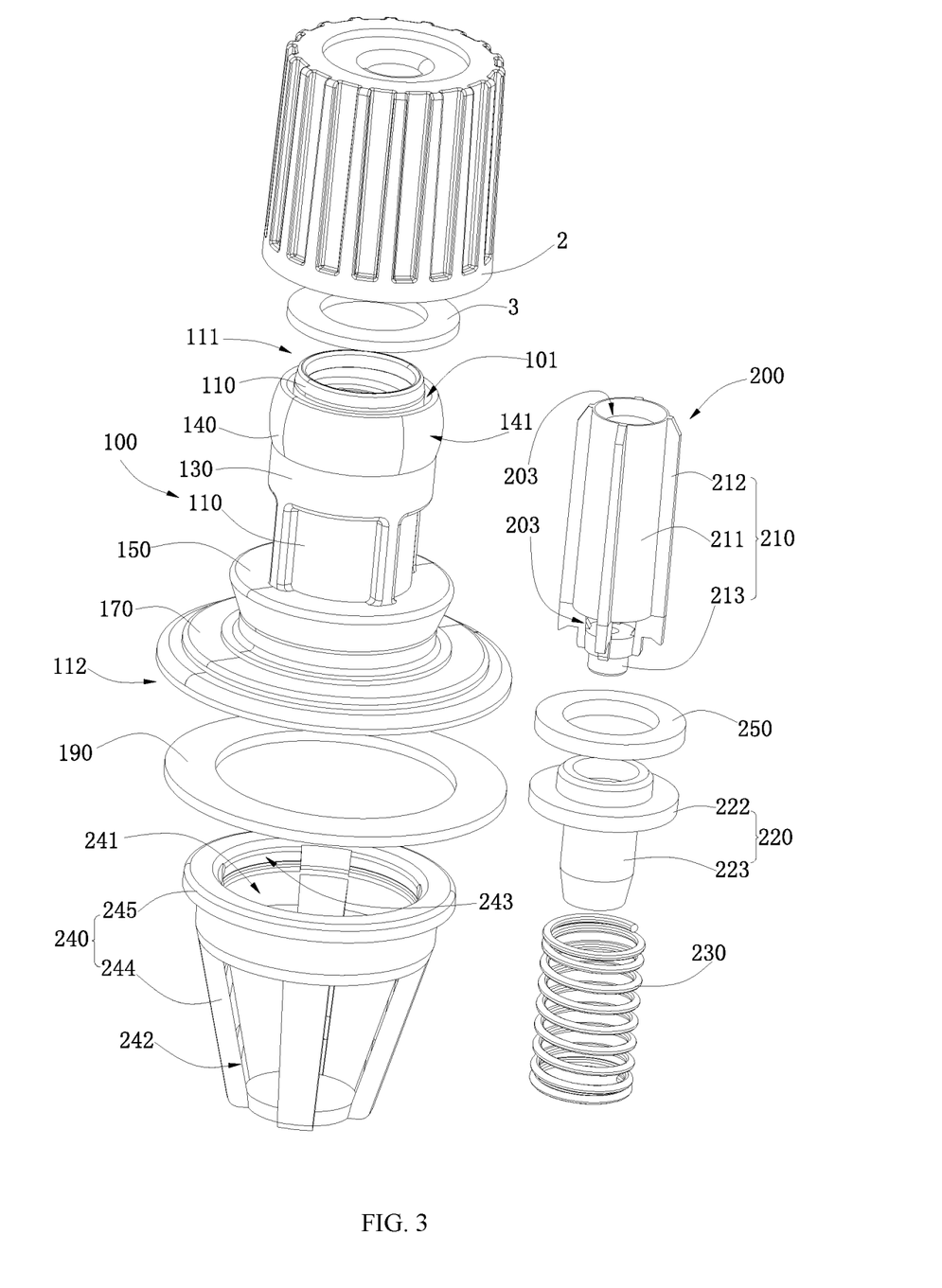
FIG. 3 is a local perspective exploded view of the anesthetic filling system provided by an embodiment of the present application.
Figure 4:
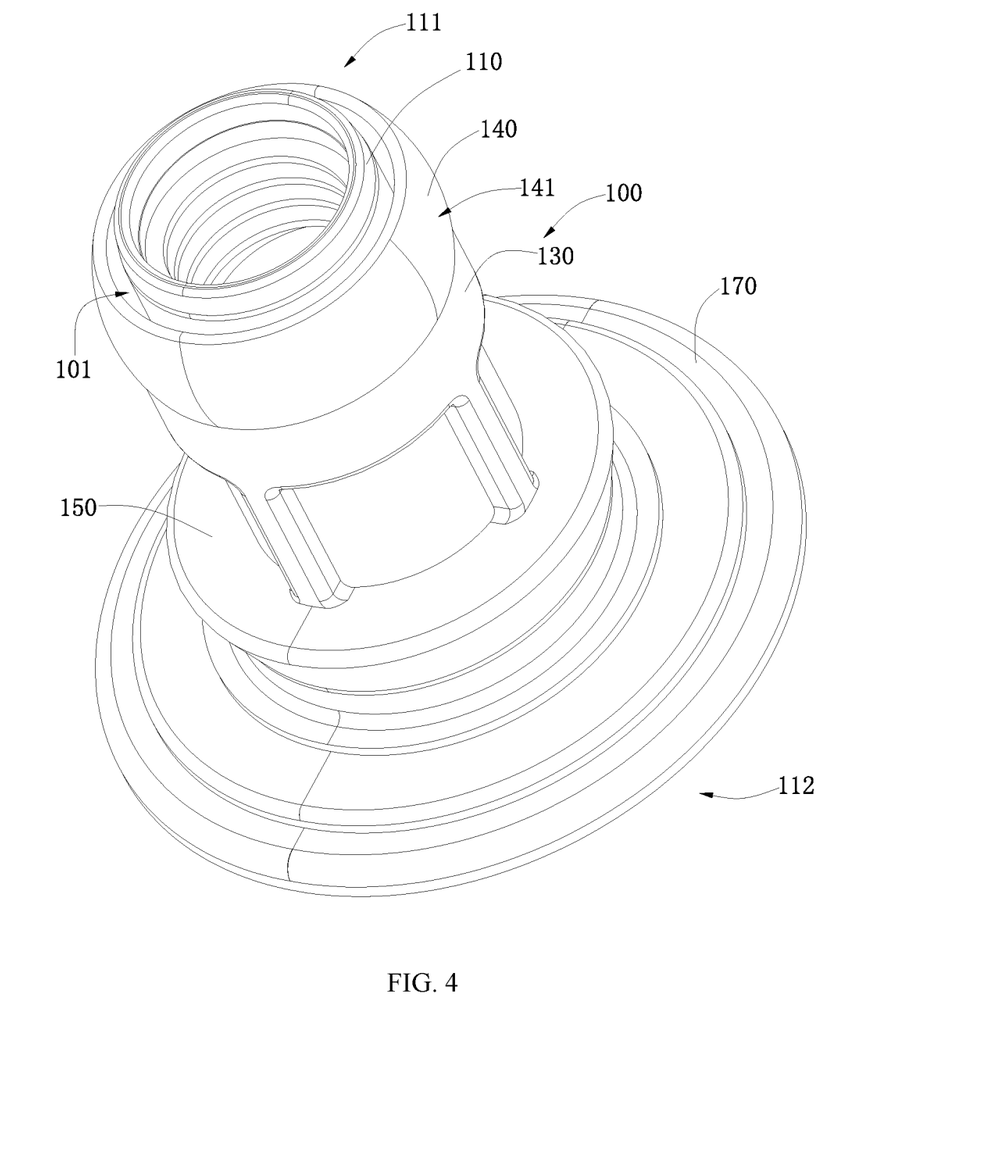
FIG. 4 is a perspective view of a drug guiding structure provided by an embodiment of the present application.

Please refer to FIGS. 2-3, further, the drug guiding structure 100 adopts a drug guiding structure 100 that is formed by polyamide (PA) plastic materials. In this way, the accuracy of the tolerance for the injection mold ensures the stability of the insertion-pull force, which further decreases the insertion-pull force between the drug guiding structure 100 and the evaporator 5, and further improves the processing efficiency of the drug guiding structure 100.

Please refer to FIGS. 2-5, further, the drug guiding structure 100 further comprises a support base 150 that is connected to the outer pipe wall of the drug guiding pipe 110 and is formed by radially extending the outer pipe wall of the drug guiding pipe 110 outwards. The support base 150 is located at an end part of the drug guiding pipe 110 away from the seal pipe 130 and abuts against the evaporator 5 during the open state. In this way, excess insertion of the drug guiding structure 100 into the filling port 51 is effectively avoided.

Please refer to FIGS. 2-3, further, the valve core assembly 200 comprises a push member 210, a sealing structural member 220, an elastic member 230, and a support 240 that is provided inside the container 6. The support 240 is fixed at the second pipe end 112, the support 240 has an open cavity 241 and at least one perfusion mouth 242 communicating with the open cavity 241, the second pipe end 112 and the sealing structural member 220 are both located inside the open cavity 241, the elastic member 230 drives the sealing structural member 220 to move towards the second pipe end 112 under the action of an elastically restoring force thereof in order to block an opening of the second pipe end 112, the push member 210 is located inside a cavity of the drug guiding pipe 110, the push member 210 is exerted with a force from the evaporator 5 towards the second pipe end 112 during the open state in order to overcome the elastically restoring force of the elastic member 230 and push the sealing structural member 220 therefore removing the blocking between the sealing structural member 220 and the second pipe end; and the drug guiding pipe 110 and the push member 210 together form a drug guiding channel for allowing the anesthetic to pass through.

Please refer to FIGS. 2-3, the drug guiding channel 201 comprises a drainage chamber 202 and a diversion chamber 203 for allowing the anesthetic to be fluently introduced to the filling port 51 of the evaporator 5.

Specifically, the push member 210 comprises a push rod 211 and at least two flow guide plates 212 connected with a side wall of the push rod 211, one end of the push rod 211 is supported by the sealing structural member 220, the at least two flow guide plates 212 are both located on a periphery of the push rod 211 and extend along a length direction of the push rod 211; any adjacent two flow guide plate 212, a part of the sidewall of the push rod 211 that is located between the two flow guide plates 212, and a part of an inner pipe wall of the drug guiding pipe 110 that is located between the two flow guide plates 212 together form a drainage chamber 202 for allowing the anesthetic to pass through. In this way, a contact area between the push member 210 and the cavity of the drug guiding pipe 110 is minimized, thus reducing the abrasion between the cavity of the drug guiding pipe 110 and the push member 210.

Particularly, the diversion chamber 203 that allows the anesthetic to pass through penetrates through one end of the push member 210 facing the filling port 51 and the other end of the push member 210 away from the filling port 51.

As shown in FIGS. 2-3, further, the valve core assembly 200 further comprises an annular first seal shim 250, and the first seal shim 250 is made from ethylene-vinyl acetate copolymer (EVA) material and fixed on a surface of the sealing structural member 220 that faces the second pipe end 112 therefore being pressed between the sealing structural member 220 and the second pipe end 112 during the closed state. In this way, the sealing property of the opening of the second pipe end 112 is improved.

Figure 5:
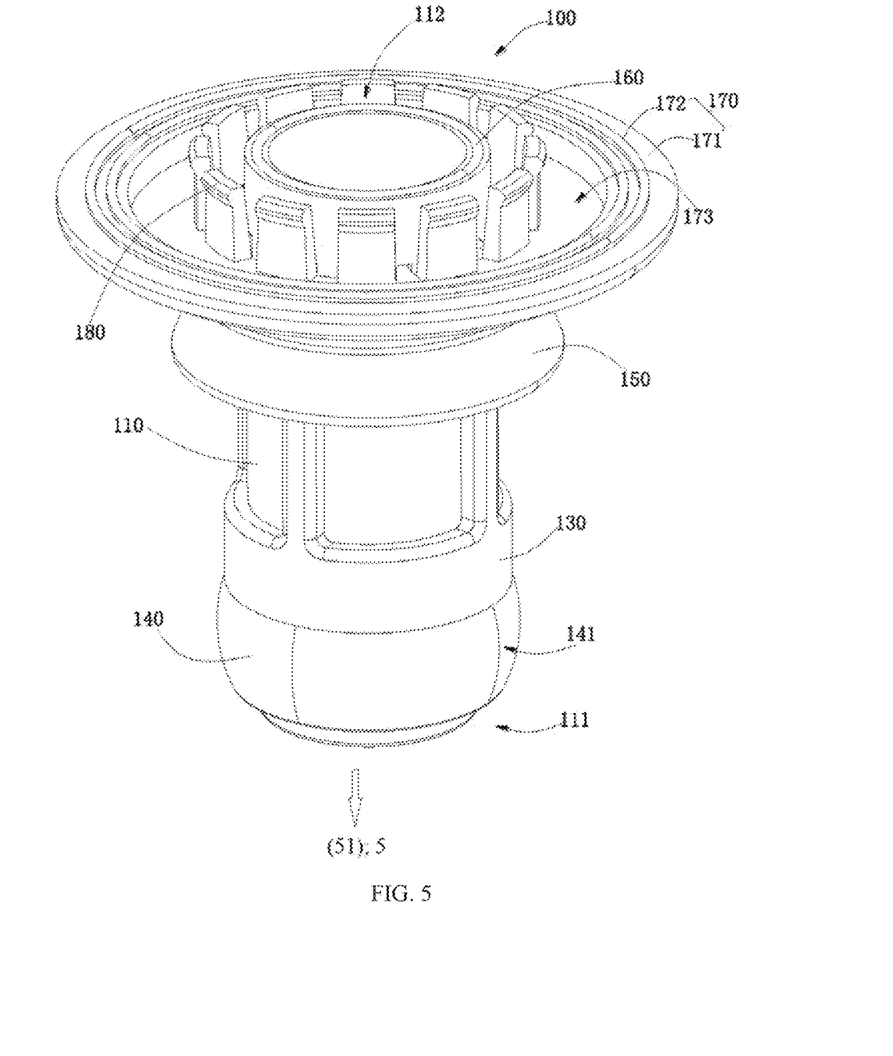
FIG. 5 is another perspective view of the drug guiding structure provided by an embodiment of the present application.

Please refer to FIGS. 2-3, and 5, further, the drug guiding structure 100 further comprises a first protrusion ring 160 that is connected with an end side of the drug guiding pipe 110 that faces the sealing structural member 220, at least one first protrusion ring 160 is provided and arranged spacedly, each of the at least one first protrusion ring 160 abut against the first seal shim 250 during the closed state. In this way, the sealing property of the opening of the second pipe end 112 is further improved.

Please refer to FIGS. 2-3, further, the push member 210 comprises a positioning block 213 connected to the end of the push rod 211, the positioning block 213 is located at the end side of the push rod 211 that faces the sealing structural member 220, the surface of the sealing structural member 220 that faces the positioning block 213 defines a positioning groove 221 that matches a shape of the positioning block 213, and the positioning block 213 is inserted into the positioning groove 221. In this way, it is convenient to realize fast assembly of the push member.

In this embodiment, the sealing structural member 220 comprises a circular plate 222 and a guiding column 223 that is connected with one side of the circular plate 222, the above elastic member 230 is a spiral spring, the spiral spring is sheathed on the guiding column 223 with one end thereof abutting against the side of the circular plate 222 and the other end thereof abutting against a bottom of the open cavity 241. The other side of the circular plate 222 that is away from the guiding column 223 defines the positioning groove 221 towards the guiding column 223. In this way, because the guiding column 223 is inserted in the spiral spring and functions in guiding, the spiral spring can be compressed or expanded along the length direction of the guiding column 223, thus improving the stability of the spiral spring.

Please refer to FIGS. 2-5, further, the drug guiding structure 100 comprises a circular-shaped flange 170 fixed inside the container 6, the flange 170 is sheathed outside an end of the drug guiding pipe 110 away from the seal pipe 130 and is connected to the drug guiding pipe 110. The flange 170 and the support 240 are in snap fit. In this way, on one hand, it is convenient to fast assemble and disassemble the support 240, and on the other hand, the stability of the support 240 is improved.

In this embodiment, the flange 170 is connected with a bottom end of the support base 150.

Please refer to FIGS. 2-3 and 5, further, the drug guiding structure 100 comprises clasps 180 connected to the flange 170, the number of the clasps 180 is plural and the clasps are uniformly arranged around the drug guiding pipe 110 and on a surface of the flange 170 facing the container 6, the support 240 defines an annular slot 243 on an inner wall of the open cavity 241, and all the clasps 180 are inserted into the open cavity 241 and in snap fit with the annular slot 243.

Please refer to FIGS. 2-3, further, the drug guiding structure 100 further comprises a second seal shim 190 that is pressed between the flange 170 and the container 6 and is ring-shaped. The second seal shim 190 is made from EVA material. In this way, the sealing property between the flange 170 and the container 6 is improved.

Please refer to FIGS. 2-3 and 5, further, the flange 170 comprises a main plate 171 and a second protrusion ring 172 connected with a surface of the main plate 171 facing the container 6, at least one second protrusion ring 172 is provided and arranged spacedly, each of the at least one second protrusion ring 172 abut against the second seal shim 190, which further improves the sealing property between the flange 170 and the container 6.

In this embodiment, the surface of the main plate 171 facing the container 6 is provided with an accommodation groove 173, the drug guiding pipe 110 passes through the accommodation groove 173, and each of the clasps 180 are connected with a bottom of the accommodation groove 173. The support 240 comprises a main support 244 and a lug 245 connected with the main support 244, the main support 244 has the above-described open cavity 241 and the perfusion mouths 242, the lug 245 is ring-shaped and sheathed on a periphery of the main support 244 at an open end of the open cavity 241, and the lug 245 and the open end of the main support 244 are inserted into the accommodation groove 173 and the lug 245 abut against the container 6.

Figure 1:
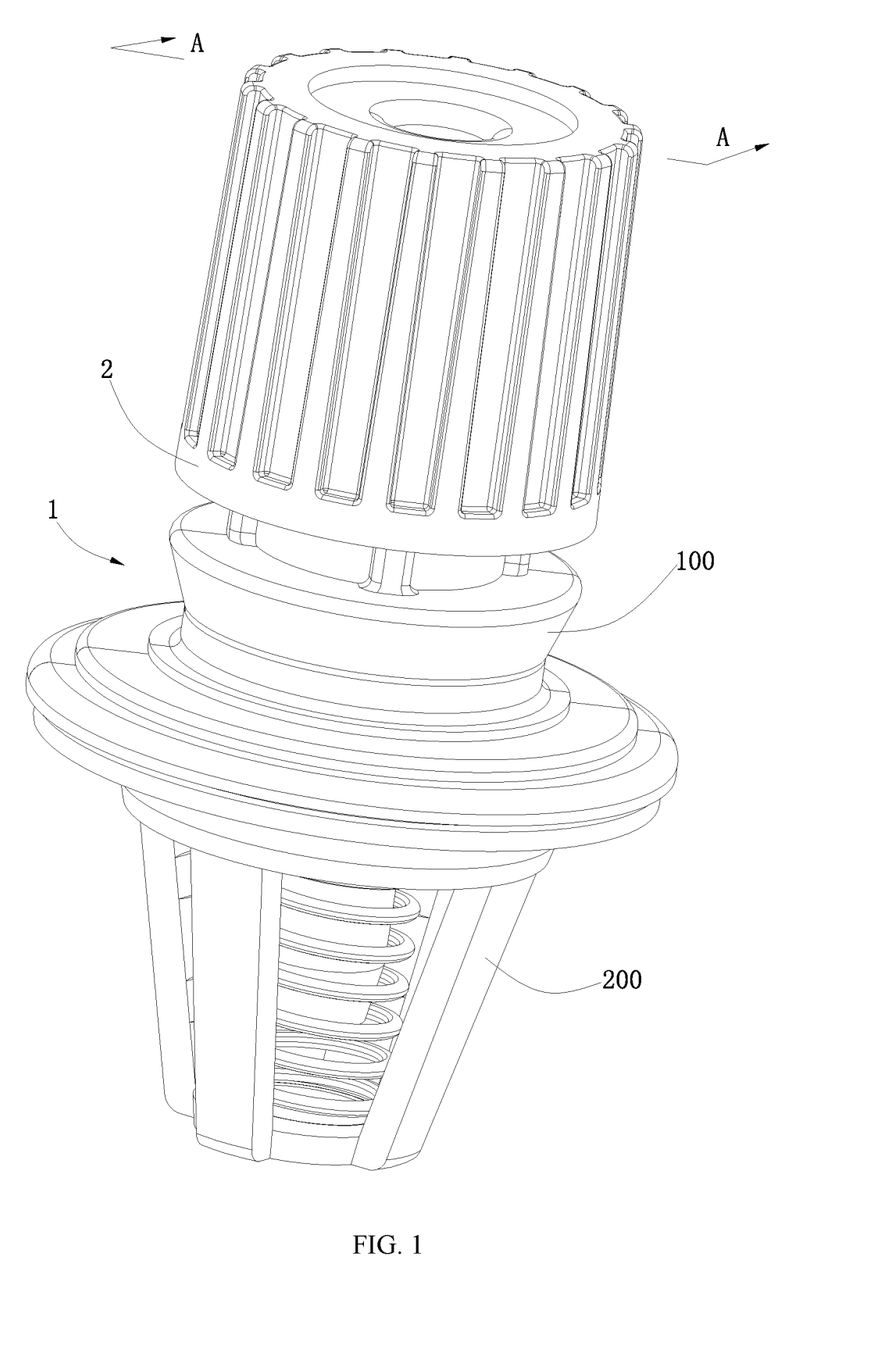
FIG. 1 is a local perspective view of an anesthetic filling system in a closed state provided by an embodiment of the present application.

Please refer to FIGS. 1-3, the present application further provides an anesthetic filling system 7, configured to connect with the evaporator 5 to introduce the anesthetic to the evaporator 5. The anesthetic filling system 7 comprises the container 6 and the above-described connecting valve structure 1. The container 6 comprises a cavity accommodated with the anesthetic and the drug outlet communicating with the cavity, the connecting valve structure 1 is fixed at the drug outlet and in seal fit with the drug outlet.

In this embodiment, when the above-described connecting valve structure 1 is applied to the anesthetic filling system 7, the insertion-pull force between the connecting valve structure 1 and the evaporator 5 is effectively decreased, which is convenient for the medical staff to operate, and further improve the sealing property between the connecting valve structure 1 and the drug filling system, thereby improving the transferring efficiency of the anesthetic. The anesthetic filling system 7 is primarily used to accommodate, but is not limited to, the desflurane.

Please refer to FIGS. 2-3, the anesthetic filling system 7 further comprises a lid 2, and the lid is used to cover an end part of the drug guiding structure 100 away from the container 6 during the closed state.

In this embodiment, because a boiling point of the desflurane is 22.8° C., which approaches the room temperature, and it is therefore indicated that a part of the desflurane presents in the gas state at the room temperature. When the valve core assembly 200 is in the closed state, it is required to cover the end part of the drug guiding structure 100 away from the container 6 by the lid 2, in this way, on the one hand, a barrier for preventing the loss of the anesthetic (desflurane) is provided, and on the other hand, impurities which may otherwise pollute the connecting valve structure 1 are prevented from inside the connecting valve structure 1.

Please refer to FIG. 2 and FIG. 3, further, the anesthetic filling system 7 further comprises a seal ring 3, the seal ring 3 is fixed inside lid 1 and is pressed between the lid and the end part of the drug guiding structure 100 away from the container 6. In this way, on the one hand, the atmospheric air is prevented from entering the connecting valve structure 1 or polluting the remaining anesthetic in the connecting valve structure, and on the other hand, the anesthetic inside the connecting valve structure 1 is prevented from leaking out, thus improving the sealing property of the drug guiding structure 100. The seal ring 3 adopts the EVA material.

Figure 6:
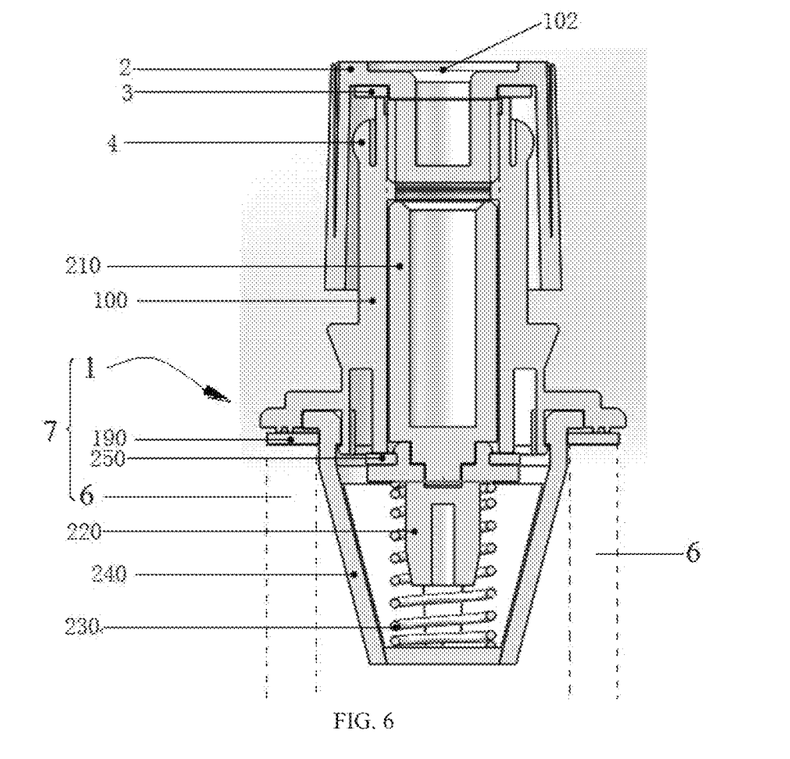
FIG. 6 is a front view of a local sectional view of the anesthetic filling system provided by an embodiment of the present application.

A specific embodiment is provided for explanation, please refer to FIG. 6, the present application provides an anesthetic filling system 7 comprising a drug receiving port 102, the drug guiding structure 100, and the push member 210. The drug receiving port 102 is provided thereon with the lid 2. An inner side of the lid 2 is provided with the seal ring 3, an upper part of the drug guiding structure 100 is provided with a seal structure 4, the push member 210 is inserted into the drug guiding structure 10, a joint part between the drug guiding structure 100 and the support 240 is provided with the second seal shim 190, a joint part between the push member 210 and the sealing structural member 220 is provided with the first seal shim 250, the elastic member 230 (spring) is sheathed on the sealing structural member 220, the upper part of the drug guiding structure 100 is provided with the pressure stabilizing groove for arrangement of the seal structure 4.

In the anesthetic filling system 7 provided by the present application, the seal structure 4 adopts an ear-shaped plastic material which can be directed inserted into the filling port 51 of the evaporator 5, the sealing projection ring is in interference fit, and a back pressure of the air pressure realizes excellent sealing property; the drug receiving port 102 is inserted into the filling port 51 of the evaporator 5 after the lid 2 is threaded therefrom; a push member 210 at the drug receiving port 102 and a rod at the filling port 51 of the evaporator 5 mutually pushes their separate elastic members to be compressed; the sealing structural member 220 of the drug receiving port 102 is pushed downwards so that the sealing structural member 220 is separated from the drug guiding structure 110, the seal state is interrupted, and the drug liquid flows out of the drug container 6; and the sealing of the filling port 51 of the evaporator 5 is also interrupted as being pushed to separate the sealing end, thus allowing the drug liquid to flow inside the evaporator 5.

The aforementioned embodiments are only preferred embodiments of the present application, and are not intended to limit the present application. It will be apparent to those skilled in the art that various changes and modifications of the present application may be made. Any modification, equivalent replacement, improvement, and so on, which are made within the spirit and the principle of the present application, should be included in the protection scope of the present application.

The invention claimed is:

1. A connecting valve structure, which is configured to connect an evaporator and a container containing an anesthetic so as to introduce the anesthetic to the evaporator, and the evaporator being provided with a filling port; wherein,
the connecting valve structure comprises a drug guiding structure and a valve core assembly;
the drug guiding structure comprises a drug guiding pipe that is provided with a first pipe end configured to form an insertion fit with the filling port and a second pipe end communicating with an inner part of the container, a connecting ring that is integrally connected with an outer pipe wall of the drug guiding pipe and is formed by radially extending the outer pipe wall of the drug guiding pipe outwards, and a seal pipe that is integrally connected to the connecting ring and formed by extending an outer annular surface of the connecting ring towards the filling port of the evaporator; the seal pipe is in seal fit with the filling port when the drug guiding pipe is inserted into the filling port; and the valve core assembly has an open state for opening the drug guiding pipe when the drug guiding pipe is inserted into the filling port and a closed state for blocking the drug guiding pipe when the drug guiding pipe is pulled out of the filling port;
wherein, an inner pipe wall of the seal pipe, a surface of the connecting ring facing towards the first pipe end, and an outer pipe wall of the drug guiding pipe opposite to the seal pipe together form a pressure stabilizing groove configured to equilibrate pressure in the container and the evaporator during the open state.

2. The connecting valve structure of claim 1, wherein the drug guiding structure further comprises a sealing protection ring that is integrally connected to an outer pipe wall of the seal pipe and is formed by radially extending the outer pipe wall of the seal pipe outwards, a shape of a cross section of the sealing projection ring has a convex curve that is convex to a direction away from the seal pipe.

3. The connecting valve structure of claim 2, wherein the convex curve is an arc.

4. The connecting valve structure of claim 1, wherein the drug guiding structure adopts a drug guiding structure that is formed by polyamideplastic materials.

5. The connecting valve structure of claim 1, wherein, the drug guiding structure further comprises a support base that is connected to the outer pipe wall of the drug guiding pipe and is formed by radially extending the outer pipe wall of the drug guiding pipe outwards, and the support base is located at an end part of the drug guiding pipe away from the seal pipe and abuts against the evaporator during the open state.

6. The connecting valve structure of claim 1, wherein, the valve core assembly comprises a push member, a sealing structural member, an elastic member, and a support that is provided inside the container; the support is fixed at the second pipe end, the support has an open cavity and at least one perfusion mouth communicating with the open cavity, the second pipe end and the sealing structural member are both located inside the open cavity, the elastic member drives the sealing structural member to move towards the second pipe end under the action of an elastically restoring force thereof in order to block an opening of the second pipe end, the push member is located inside a cavity of the drug guiding pipe, the push member is exerted with a force from the evaporator towards the second pipe end during the open state in order to overcome the elastically restoring force of the elastic member and push the sealing structural member therefore removing the blocking between the sealing structural member and the second pipe end; and the drug guiding pipe and the push member together form a drug guiding channel for allowing the anesthetic to pass through.

7. The connecting valve structure of claim 6, wherein, the push member comprises a push rod and at least two flow guide plates connected with a side wall of the push rod, one end of the push rod is supported by the sealing structural member, the at least two flow guide plates are both located on a periphery of the push rod and extend along a length direction of the push rod; and any adjacent two flow guide plate, a part of the sidewall of the push rod that is located between the two flow guide plates, and a part of an inner pipe wall of the drug guiding pipe that is located between the two flow guide plates together form a drainage chamber for allowing the anesthetic to pass through, and the drug guiding channel comprise the drainage chamber.

8. The connecting valve structure of claim 7, wherein, the push member comprises a positioning block connected to the end of the push rod, the positioning block is located at the end side of the push rod that faces the sealing structural member, the surface of the sealing structural member that faces the positioning block defines a positioning groove that matches a shape of the positioning block, and the positioning block is inserted into the positioning groove.

9. The connecting valve structure of claim 6, wherein, a diversion chamber that allows the anesthetic to pass through penetrates through one end of the push member facing the filling port and the other end of the push member away from the filling port, and the drug guiding channel comprises the diversion chamber.

10. The connecting valve structure of claim 6, wherein, the valve core assembly further comprises an annular-shaped first seal shim, and the first seal shim is made from an ethylene-vinyl acetate copolymer material and fixed on a surface of the sealing structural member that faces the second pipe end therefore being pressed between the sealing structural member and the second pipe end during the closed state.

11. The connecting valve structure of claim 6, wherein, the drug guiding structure comprises a circular-shaped flange fixed inside the container, the flange is sheathed outside an end of the drug guiding pipe away from the seal pipe and is connected to the drug guiding pipe, and the flange and the support are in snap fit.

12. The connecting valve structure of claim 11, wherein, the drug guiding structure comprises clasps connected to the flange, the number of the clasps is plural and the clasps are uniformly arranged around the drug guiding pipe and on a surface of the flange facing the container, the support defines an annular slot on an inner wall of the open cavity, and all the clasps are inserted into the open cavity and in snap fit with the annular slot.

13. The connecting valve structure of claim 11, wherein, the drug guiding structure further comprises a second seal shim that is pressed between the flange and the container and is ring-shaped, and the second seal shim is made from an ethylene-vinyl acetate copolymer material.

14. An anesthetic filling system, configured to connect with the evaporator to introduce an anesthetic to the evaporator, wherein the anesthetic filling system comprises a container and the connecting valve structure of claim 1, the container comprises a cavity accommodated with the anesthetic and a drug outlet communicating with the cavity, and the connecting valve structure is fixed at the drug outlet and in seal fit with the drug outlet.

15. The anesthetic filling system of claim 14, further comprising a lid, and the lid is used to cover an end part of the drug guiding structure away from the container during the closed state.

16. The anesthetic filling system of claim 15, wherein, the anesthetic filling system further comprises a seal ring, the seal ring is fixed inside lid and is pressed between the lid and the end part of the drug guiding structure away from the container.

* * * * *